United States Patent [19]

Arakawa et al.

[11] Patent Number: 5,308,695
[45] Date of Patent: May 3, 1994

[54] ADHESIVE TAPES FOR MEDICAL OR SANITARY USE

[75] Inventors: Masaaki Arakawa; Hidehiko Murata; Takaaki Moriyama; Kazuo Suenaga, all of Osaka, Japan

[73] Assignee: Nitto Denko Corporation, Osaka, Japan

[21] Appl. No.: 44,047

[22] Filed: Apr. 8, 1993

Related U.S. Application Data

[63] Continuation of Ser. No. 785,869, Nov. 1, 1919, Pat. No. 5,264,281, which is a continuation of Ser. No. 423,286, Oct. 18, 1989, abandoned.

[30] Foreign Application Priority Data

Oct. 18, 1988 [JP] Japan .................... 63-135859
Apr. 6, 1989 [JP] Japan .................... 1-41040
Sep. 26, 1989 [JP] Japan .................... 1-249521

[51] Int. Cl.$^5$ ............................................. B32B 7/12
[52] U.S. Cl. ........................................ 428/354; 428/261; 428/286; 428/287; 428/343; 428/519; 428/521; 604/386; 604/387; 604/389; 604/390; 427/208.4
[58] Field of Search .............. 428/343, 354, 519, 521, 428/261, 286, 287; 604/386, 387, 389, 390; 427/208.4

[56] References Cited

U.S. PATENT DOCUMENTS

| 3,635,907 | 1/1972 | Schulze et al. | 524/726 X |
| 3,716,437 | 2/1973 | Newman et al. | 156/244 |
| 3,908,650 | 9/1975 | Dunshee et al. | 128/156 |
| 4,007,311 | 2/1977 | Harlan, Jr. | 428/463 X |
| 4,107,233 | 8/1978 | Hansen | 428/463 X |
| 4,332,858 | 6/1982 | Saitoh et al. | 428/519 X |
| 4,389,212 | 6/1983 | Tritsch | 604/389 |
| 4,424,259 | 1/1984 | Middlebrook | 428/519 X |
| 4,522,853 | 6/1985 | Szonn et al. | 604/389 X |
| 4,543,099 | 9/1985 | Bunnelle et al. | 428/152 X |
| 4,704,130 | 11/1987 | Gilding et al. | 521/50 X |
| 4,784,653 | 11/1988 | Bolton et al. | 428/354 X |
| 4,787,897 | 11/1988 | Torimae et al. | 428/355 X |
| 4,904,253 | 2/1990 | Sipinen et al. | 604/389 |
| 4,906,240 | 3/1990 | Reed et al. | 604/389 X |
| 4,919,999 | 4/1990 | Maria Van Soom | 428/354 X |
| 5,063,106 | 11/1991 | Nieuwehuize et al. | 428/343 |

FOREIGN PATENT DOCUMENTS

2830536 1/1980 Fed. Rep. of Germany .
63-112704 5/1988 Japan .

OTHER PUBLICATIONS

Penn, W. S. PVC Technology, p. 41.

Primary Examiner—Daniel Zirker
Attorney, Agent, or Firm—Sughrue, Mion, Zinn, Macpeak & Seas

[57] ABSTRACT

The present invention provides a medical or sanitary adhesive tape comprising a support composed of a laminate structure of a first layer containing a thermoplastic elastomer and a second layer comprising a plastic film or nonwoven fabric, and an adhesive layer formed at least one surface of said support. The adhesive tape possesses advantages that is endowed with properties of both softness and elasticity, gentle to the skin and excellent in handling and processing characteristics.

1 Claim, 2 Drawing Sheets

ADHESIVE TAPES FOR MEDICAL OR SANITARY USE

This is a continuation of application Ser. No. 07/785,869, filed Nov. 1, 1991, now U.S. Pat. No. 5,264,281 which is a continuation of application Ser. No. 07/423,286 filed Oct. 18, 1989, now abandoned.

BACKGROUND OF THE INVENTION

1. Field of the Invention

The present invention relates to adhesive tapes for medical or sanitary use and the like; and, more particularly, to adhesive tapes which can be advantageously used as fastener fixing tapes for paper diapers or as non-slip tapes for sanitary napkins, etc.

2. Description of the Prior Art

Adhesive tapes for medical or sanitary use, etc. are used in contact with the human body. Therefore, feeling and softness are to prevent redness, rash, lacerated wound, etc. to the skin.

In response to such demand, various improvements have been made on tape supports. For example, there is known an adhesive tape using as a tape support a film composed of a mixture of one or more members selected from ethylene-vinyl acetate copolymer, polyethylene or ethylene-propylene copolymer and polypropylene (Japanese Patent Application Laid-Open No. 63-112704).

However, such a tape still causes redness, though occurrence of rashes or lacerated wounds is improved. In addition, since processing characteristics upon preparation are also taken into account, the tape

SUMMARY OF THE INVENTION

The present invention has been made to solve such problems and provides adhesive tapes for medical or sanitary use, etc. which are endowed with properties of both softness and elasticity are gentle to the skin and exhibit excellent handling and processing characteristics.

That is, the present invention relates to a medical or sanitary adhesive tape comprising a support composed of a laminate structure of a first layer containing a thermoplastic elastomer and a second layer comprising a plastic film or nonwoven fabric, and an adhesive layer formed on at least one surface of the support.

BRIEF DESCRIPTION OF THE DRAWINGS

In FIGS. 1-8:

Figure 1:
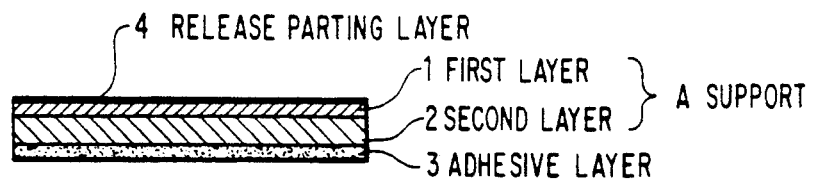
FIGS. 1 through 7 are cross sectional views showing working examples of the adhesive tape according to the present invention.

| A | support |
| --- | --- |
| 1 | first layer |
| 2 | second layer |
| 3 | adhesive layer |

DETAILED DESCRIPTION OF THE PREFERRED EMBODIMENTS

The first layer, which constitutes the support used in the present invention, is an elastic film composed of thermoplastic elastomer or mainly composed of the elastomer. It is desired to use a thermoplastic elastomer showing a permanent compression strain of 5 to 100%, preferably 20 to 60% and having Shore hardness of not less than 20 and not more than D70, preferably A40 to A90. The permanent compression strain as used herein refers to that measured at compressibility of 25% and 70° C. for 22 hours in accordance with JIS K6301. The Shore hardness is determined in accordance with ASTM D2240. By setting the values of permanent compression strain and Shore hardness in the ranges described above in the present invention, softness and elasticity of the adhesive tape can be obtained.

Specific examples of the thermoplastic elastomer described above include polyolefin type elastomers having a hard segment is polyethylene, polypropylene, etc. and a soft segment of ethylenepropylene diene monomer, ethylenepropylene monomer, etc.; polystyrene type elastomer in which the hard setment is polystyrene and the soft segment is butadiene rubber, isoprene rubber, hydrogenated butadiene rubber, etc.; polyvinyl chloride type elastomer in which the hard segment is polyvinyl chloride, etc. and the soft segment is a plasticizer such as 2-ethylhexyl phthalate (dioctyl phthalate), etc. or a polymer blend such as NBR, partially cross-linked NBR, etc., rubber such as modified PVC, etc.; polyester type elastomer in which the hard segment is polyester and the soft segment is polyether or polyester; polyurethane type elastomer in which the hard segment is polyurethane and soft segment is polyester or polyether; chlorinated polyethylene type elastomer in which the hard segment is block type chlorinated polyethylene and soft segment is random chlorinated polyethylene, etc. These elastomers may be used singly or in combination.

In addition, by using as the first layer an elastic film comprising a mixture of the thermoplastic elastomer described above and one or more thermoplastic resins selected from polyethylene, polypropylene and ethylene-vinyl acetate copolymer, adhesion to the second layer, which will be later described, can also be improved. As the ethylene-vinyl acetate copolymer, a copolymer having a vinyl acetate content of 5% or less is generally preferably used. The thermoplastic resin as used herein refers to crystalline resin having a storage elastic modulus $G'$ of $10^8$ or more at normal temperature (20° C.) which does not show rubber elasticity at normal temperature (20° C.).

The weight ratio of the thermoplastic elastomer to the thermoplastic resin in this case is generally in the range of 1:9 to 9:1, preferably 5:5 to 1:9.

In the present invention, it is particularly preferred to use as the first layer the hydrogenated product of block copolymer represented by the general formula:

$$A-(B-A)n$$

or a mixture of the block copolymer with polyolefin type thermoplastic resin such as polyethylene, polypropylene, etc.

In the formula, A is a polymer block of monovinyl-substituted aromatic hydrocarbon such as polystyrene, poly-α-methylstyrene, etc.; B is an elastomeric polymer block of conjugated diene such as butadiene, isoprene, etc.; n is 1 to 4; and a weight ratio of A to B is 10/90 to 50/50. A weight average molecular weight of this hydrogenated block copolymer is approximately 30,000 to 300,000 and a hydrogenated amount is approximately 70 to 95% based on the diene component (component B).

For hydrogenation of the conjugated diene polymer, there is a method which comprises dissolving the polymer in an inert hydrocarbon solvent, e.g., cyclohexane, etc., adding cobalt, nickel or the like reduced using a catalyst such as an alkyl aluminum, etc. to the solution, and reacting for about 10 to about 60 minutes generally at 25 to 50° C. under pressure of, e.g., 5 to 40 kg/cm$^2$ hydrogen.

Further, in using the mixture of this hydrogenated block copolymer and polyolefin type thermoplastic resin, it is preferred to use 5 to 100 parts by weight of the polyolefin type thermoplastic resin based on 100 parts by weight of the hydrogenated block copolymer.

As the second layer in the present invention, a plastic film composed of a mixture of one or more thermoplastic resins selected from polyethylene, ethylene-propylene copolymer or ethylene-vinyl acetate copolymer and polypropylene or polypropylene alone is used. In this case, it is desired that a weight ratio of the thermoplastic resin to polypropylene be in the range of 0:10 to 9:1, preferably 4:6 to 6:4. The thermoplastic resin as used herein refers to crystalline resin having a storage elastic modulus G' of $10^8$ or more at normal temperature (20° C.) which does not show rubber elasticity at normal temperature (20° C.).

As the second layer, nonwoven fabric of polyester type, nylon type or polyolefin type may also be used. In order to impart elasticity thereto, it is preferred to use nonwoven fabric having a weight of at least 20 g/m$^2$. Pressure or heat may also be applied to such nonwoven fabric to further improve its strength.

In order to firmly bind it to the first layer and form a support endowed with softness and elasticity, such a second layer has toughness and elasticity properties so that it can reinforce the first layer without reducing the softness of the first layer.

A polyethylene film of approximately 1 to 100 μm may further be laminated onto one surface or both surfaces of such nonwoven fabric, whereby the transfer of the thermoplastic elastomer in the first layer and the adhesive later described can be prevented.

The support used in the present invention has a laminate structure of the first layer and the second layer described above, that is, a dual layer structure, three layered structure or more. A thickness of the support is not particularly limited but generally from 10 μm to 1 mm. A thickness ratio of the first layer to the second layer is generally from 1:1 to 1000.

The adhesive layer provided on at least one surface of the support described above is not particularly limited and ordinary adhesive of acrylic type, rubber type, styrene type, etc. can be used. Its thickness is set at approximately 5 to 500 μm. It is preferred that such an adhesive layer be attached on the second layer side of the support. With such a structure, the first layer is located on the surface and in contact with the skin. Therefore, the tape is gentle to the touch.

Furthermore, a back treating agent of a long chain alkyl type or silicone type can also be applied to at least the other surface of the support.

The adhesive tape of the present invention has a crosswise compression strength of 200 g/mm$^2$ or less, preferably 40 to 100 g/mm$^2$. By setting the crosswise compression strength within such a range, the resulting adhesive tape advantageously possesses appropriate softness and elasticity. The crosswise compression strength as used herein is determined by the method which will be explained in the examples later described.

FIG. 1 is a cross sectional view of an example showing the adhesive tape of the present invention, wherein A is a support composed of first layer 1 and second layer 2 laminated therebeneath; adhesive layer 3 is provided on the side of such second layer 2; and 4 is a release parting agent provided on the other surface of the support A, if necessary and desired.

FIGS. 2 through 7 are cross sectional views showing other embodiments of the adhesive tape of the present invention, respectively.

Figure 2:
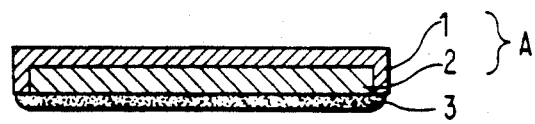

FIG. 2 shows a structure in which the first layer 1 in FIG. 1 overlaps the edges of second layer 2. In this case, the side surface of second layer 2 is not in direct contact with the skin.

Figure 3:
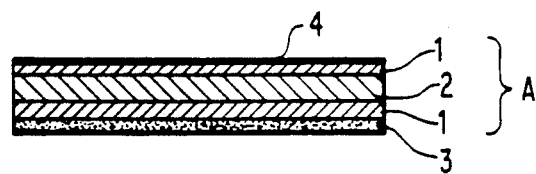

FIG. 3 shows an adhesive layer using support A composed of first layer 1 having laminated second layer 2 on both surfaces thereof.

Figure 4:
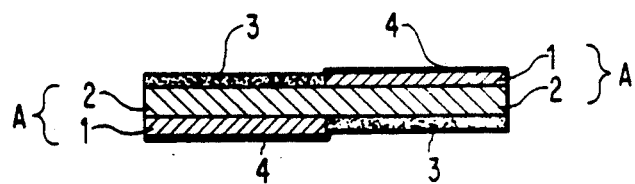

FIG. 4 shows a structure, in which about half of the tape has the same structure as in FIG. 1 and the other half has a structure that adhesive layer 3 is provided on support A, obtained by laminating first layer 1 below second layer 2. With such a difference in level between the structures, whereby the tape is foldable in half and windable into a roll shape.

Figure 5:
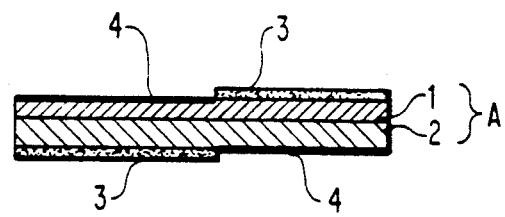

FIG. 5 shows a structure in which adhesive layer 3 is affixed below about half the width of support A, which is of first layer 1 and second layer; and, release parting layer 4 is provided on the support. The remaining half is a mirror image of the above structure.

Figure 6:
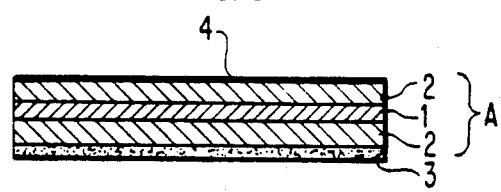

FIG. 6 shows an adhesive tape using support A having a 3 layered structure comprising first layer 1 with second layer 2 laminated on both surfaces thereof.

Figure 7:
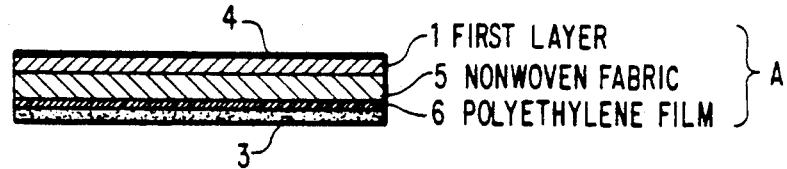

FIG. 7 shows a structure in which adhesive layer 3 is affixed via polyethylene film 6 on one surface of support A of a structure comprising first layer 1, having laminated therebeneath nonwoven fabric 5.

Figure 8:
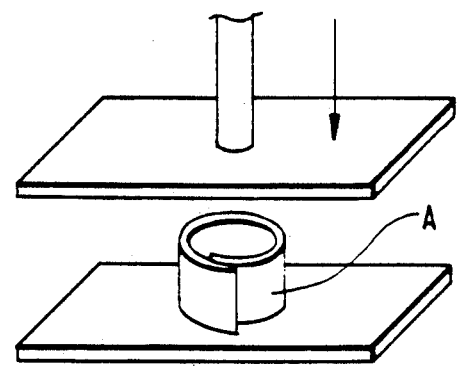
FIG. 8 is an explanatory illustration showing a method for determining crosswise compression strength of the support used in the present invention.

FIG. 8 is an explanatory illustration showing a method for determining crosswise compression strength, which is described in detail below.

Furthermore, the first layer may also be partially provided onto the second layer in an uneven state, stripe-like state or lattice-like state, while it is not shown.

The adhesive tape of the present invention can be prepared by co-extrusion, extrusion coating, lamination with heat or adhesives, or solvent coating of the respective layers.

By construction the support as a laminate structure of the first layer and the second layer, the adhesive tape of the present invention possesses softness, and is gentle to the skin but does not injure the skin even when contacted therewith. The tape exhibits excellent handling and processing properties because of this combination of softness and elasticity. Further, by disposing the first layer on the surface, the tape also feels good against the skin and is easy to grasp due to considerable surface friction.

Hereafter the present invention is described in detail by referring to the examples below.

EXAMPLES 1 through 12

Elastic films and plastic films were prepared using materials shown in Table 1 as the first and second layers, respectively. Both films were subjected to two-coat coextrusion at 200° C. through a T die to give a dual layer film.

Then an adhesive layer was provided on the plastic film side of the dual layer film to give an adhesive tape.

Further, the first layer may be formed onto nonwoven fabric by extrusion coating; and, an adhesive layer may be provided on the other surface of nonwoven fabric to give an adhesive tape.

COMPARATIVE EXAMPLES 1 THROUGH 4

Adhesive tapes were prepared in a manner similar to the Examples; except, no first layer was used.

Properties of the tapes obtained in the Examples and Comparative Examples were evaluated by the following techniques. The results are shown in Table 2.

Crosswise Compression Strength

A shown in FIG. 8, dual layer film A (65 mm×25 mm) of the support was wound up in the lengthwise direction to form a crepe (diameter of 20 mm). This crepe was put on a stand and compressed from above at 23° C. and 65% RH under 10 mm/min to determine the maximum compression strength, which was measured when the crepe began to collapse. The maximum strength was divided by the thickness of the support to obtain the crosswise compression strength.

Elasticity, Softnesss, Touch and Easy Grasp

Paper diapers using the adhesive tape as fastener fixing tapes for paper diapers were used for 20 infants. Organoleptic evaluation was performed by the following criteria.

|   | Number of infants who feel unpleasant/ 20 |
|---|---|
| ⓒ | 0/20 |
| o | 1 to 5/20 |
| Δ | 6 to 10/20 |
| x | more than 11/20 |

Rate of Redness

When paper diapers using the adhesive tape as fastener fixing tape were used for 20 infants, a rate of redness was measured.

Total Evaluation

Total evaluation was performed using the above results.

TABLE 1

(parts by weight unless otherwise indicated)

| Material | | Example | | | | | | | | | | | | Comparative Example | | | |
|---|---|---|---|---|---|---|---|---|---|---|---|---|---|---|---|---|---|
| | | 1 | 2 | 3 | 4 | 5 | 6 | 7 | 8 | 9 | 10 | 11 | 12 | 1 | 2 | 3 | 4 |
| Elastic film: | | | | | | | | | | | | | | | | | | |
| (a) | Ethylenepropylene elastomer | 100 | — | — | — | — | — | — | — | — | — | — | — | — | — | — | — |
| (b) | Styrene-butadiene block copolymer | — | 100 | — | — | — | — | — | — | — | — | — | — | — | — | — | — |
| (c) | Styrene-ethylene/butylene-styrene block copolymer | | | | | | | | | | | | | | | | |
| | $C_1$ | — | — | — | — | — | 100 | 100 | — | — | — | — | — | — | — | — | — |
| | $C_2$ | — | — | — | — | — | — | — | 100 | 100 | — | — | 100 | — | — | — | — |
| (d) | Polyester type elastomer | — | — | 100 | — | — | — | — | — | — | — | — | — | — | — | — | — |
| (e) | Urethane type elastomer | — | — | — | 100 | — | — | — | — | — | — | — | — | — | — | — | — |
| (f) | Vinyl chloride type elastomer | — | — | — | — | 100 | — | — | — | — | — | — | — | — | — | — | — |
| (g) | Polyethylene | — | — | — | — | — | 100 | 50 | 100 | — | — | — | 100 | — | — | — | — |
| (h) | Polypropylene | — | — | — | — | — | — | 50 | — | 50 | — | — | — | — | — | — | — |
| (i) | Ethylene-vinyl acetate copolymer | — | — | — | 50 | 50 | — | — | — | — | 100 | — | — | — | — | — | — |
| (j) | Ultra Low density polyethylene | — | 30 | — | — | — | — | — | — | — | — | 100 | — | — | — | — | — |
| Thickness (μm) | | 100 | 100 | 100 | 100 | 100 | 50 | 50 | 50 | 50 | 50 | 50 | 50 | — | — | — | — |
| Plastic film: | | | | | | | | | | | | | | | | | | |
| (k) | Polyethylene | 50 | 50 | — | — | — | 100 | 100 | — | 100 | 100 | 100 | — | 50 | 95 | — | — |
| (l) | Ethylene-vinyl acetaet copolymer | — | — | — | 90 | 90 | — | — | 50 | — | — | — | — | — | — | — | — |
| (m) | Ethylene-propylene copolymer | — | — | — | — | — | 10 | — | — | — | — | — | — | — | 10 | 10 | — |
| (n) | Polypropylene | 50 | 50 | 100 | 10 | 10 | 100 | 50 | 100 | 100 | 100 | 100 | — | 50 | 5 | 100 | 100 |
| Thickness (μm) | | 200 | 200 | 200 | 200 | 200 | 200 | 200 | 200 | 200 | 200 | 200 | 200 | 200 | 200 | 150 | 200 |
| Nonwoven fabric/(polyester type) (thickness 50 μm) | | | | | | | | | | | | | Weight 50 | | | | |
| Adhesive layer: Adhesive type | | sytrene | | | | | | rubber | | | | sytrene | | rubber | | | |
| Thickness (μm) | | 50 | 50 | 50 | 50 | 50 | 50 | 50 | 50 | 50 | 50 | 50 | 50 | 50 | 50 | 150 | 50 |

TABLE 2

| Item Evaluated | Example | | | | | | | |
|---|---|---|---|---|---|---|---|---|
| | 1 | 2 | 3 | 4 | 5 | 6 | 7 | 8 |
| Crosswise compression strength (g/mm²) | 50 | 55 | 143 | 63 | 56 | 68 | 89 | 62 |
| Elasticity | ⓒ | ⓒ | ⓒ | ⓒ | ⓒ | ⓒ | ⓒ | ⓒ |
| Softness | ⓒ | ⓒ | ⓒ | ⓒ | ⓒ | ⓒ | ⓒ | ⓒ |
| Touch | O | O | O | O | O | O | O | O |

TABLE 2-continued

| | | | | | | | | |
|---|---|---|---|---|---|---|---|---|
| Easiness to seize | ○ | ○ | ○ | ○ | ○ | ○ | ○ | ○ |
| Rate of redness to the skin (%) | 0 | 0 | 20 | 0 | 0 | 0 | 5 | 0 |
| Total evaluation | Excellent | Excellent | Good | Excellent | Excellent | Excellent | Good | Excellent |

| | Example | | | | Comparative Example | | | |
|---|---|---|---|---|---|---|---|---|
| Item Evaluated | 9 | 10 | 11 | 12 | 1 | 2 | 3 | 4 |
| Crosswise compression strength (g/mm$^2$) | 99 | 52 | 53 | 63 | 178 | 52 | 204 | 228 |
| Elasticity | ○ | ○ | ○ | ○ | ○ | X | X | ○ |
| Softness | ○ | ○ | ○ | ⊙ | X | ○ | △ | X |
| Touch | ○ | ○ | ○ | ○ | △ | ○ | △ | X |
| Easiness to seize | ○ | ○ | ○ | ○ | X | X | X | X |
| Rate of redness to the skin (%) | 5 | 0 | 0 | 0 | 100 | 0 | 100 | 100 |
| Total evaluation | Good | Excellent | Excellent | Excellent | Poor | Poor | Poor | Poor |

Details of the materials shown in Table 1 are as follows.

(a) Ethylenepropylene elastomer (TPE 1500 manufactured by Sumitomo Chemical Industry Co., Ltd.)

| Permanent compression strain(%): | 51 |
|---|---|
| Shore hardness: | A61 |

(b) Styrene-butadiene type block copolymer (CALIFLEX TR-1102 manufactured by Shell Co., Ltd.)

| Permanent compression strain(%): | 30–50 |
|---|---|
| Shore hardness: | A62 |
| Weight ratio of styrene/butadiene: | 28/72 |

(c) Styrene-ethylene/butylene-styrene block copolymer $c_1$ (KRATON G-1652 manufactured by Shell Co., Ltd.)

| Permanent compression strain(%) | 30–50 |
|---|---|
| Shore hardness: | A75 |
| Weight ratio of styrene/rubber: | 29/71 |

$c_2$ (KRATON G-1657 manufactured by Shell Co., Ltd.)

| Permanent compression strain(%): | 30–50 |
|---|---|
| Shore hardness: | A65 |
| Weight ratio of styrene/rubber: | 14/86 |

(d) Polyester type elastomer (P-40H manufactured by Toyobo Co., Ltd.)

| Permanent compression strain(%): | 50 |
|---|---|
| Shore hardness: | D38 |

(e) Urethane type elastomer (PANDEX T-5010 manufactured by Dainippon Ink Industries, Inc.)

| Permanent compression strain(%): | 30 |
|---|---|
| Shore hardness: | D53 |

(f) Vinyl chloride type elastomer (SUMIFLEX manufactured by Sumitomo Bakelite Co., Ltd.)

| Permanent compression strain(%): | 47 |
|---|---|
| Shore hardness: | A62 |

(g) Polyethylene (NUCG-5220 manufactured by Nippon Unica Co., Ltd.)

| MI (dg/min): | 2.0 |
|---|---|
| Density (g/m$^2$): | 0.919 |

(h) Polypropylene (HI-POL B-230 manufactured by Mitsui Petrochemical Co., Ltd.)

| MFR (g/10 mins): | 0.5 (ASTM D1238) |
|---|---|
| Density (g/m$^2$): | 0.91 |

(i) Ethylene-vinyl acetate copolymer (EVAFLEX EV-360 manufactured by Mitsui Petrochemical Co., Ltd.)

| Vinyl acetate content: | 25% |
|---|---|
| MI (dg/min): | 2.0 |
| Density (g/m$^2$): | 0.94 |

(j) Ultra low density polyethylene (YUKALON SELL X-139 manufactured by Mitsubishi Petrochemical Co., Ltd.)

| MFR (g/10 mins): | 2 (JIS K6760) |
|---|---|
| Density (g/m$^2$): | 0.90 |

(k) Polyethylene (NUCG-5220 manufactured by Nippon Unica Co., Ltd.)

| MI (dg/min): | 2.0 |
|---|---|
| Density (g/m$^2$) | 0.919 |

(l) Ethylene-vinyl acetate copolymer (V-141 manufactured by Nippon Petrochemical Co., Ltd.)

| MFR (g/10 mins): | 0.3 (JIS K6760) |
|---|---|
| Density (g/m$^2$): | 0.929 |

(m) Ethylene-propylene copolymer (SOFTREX C-9001 manufactured by Nippon Petrochemical Co., Ltd.)

| MFR (g/10 mins): | 0.5 (ASTM D1238) |
|---|---|

| | -continued |
|---|---|
| Density (g/m²): | 0.90 |

(n) Polypropylene
same as (h)

While the invention has been described in detail and with reference to specific embodiments thereof, it is apparent to one skilled in the art that various changes and modifications can be made therein without departing from the spirit and the scope of the invention.

What is claimed is:

1. A medical or sanitary adhesive tape comprising:
   (a) a support having a laminate structure comprising:
      (1) a first layer of an elastic film comprising one of or a mixture of at least two thermoplastic elastomers selected from the group consisting of: polyolefin elastomers having a hard segment of polyethylene or polypropylene and a soft segment of ethylenepropylene diene monomer or ethylenepropylene monomer; polystyrene elastomers having a hard segment of polystyrene and a soft segment of butadiene rubber, isoprene rubber, or hydrogenated butadiene rubber; polyester elastomers having a hard segment of polyester and a soft segment of polyether or polyester; and chlorinated polyethylene elastomers having a hard segment of block chlorinated polyethylene and a soft segment of randomly chlorinated polyethylene, wherein said thermoplastic elastomer used in the first layer has a permanent compression strain of 5 to 100% and a Shore hardness of not less than A20 and not more than D70;
      (2) a second layer comprising a plastic film or a nonwoven fabric wherein the crosswise compression strength of said support is not greater than 200 g/mm²; and
   (b) an adhesive layer formed on at least one surface of said support.

* * * * *